United States Patent [19]

Bertus et al.

[11] 4,209,453
[45] Jun. 24, 1980

[54] ANTIMONY TRIS(DIHYDROCARBYL PHOSPHITE) AND PREPARATION THEREOF

[75] Inventors: Brent J. Bertus; Dwight L. McKay; Harold W. Mark, all of Bartlesville, Okla.

[73] Assignee: Phillips Petroleum Company, Bartlesville, Okla.

[21] Appl. No.: 926,695

[22] Filed: Jul. 25, 1978

[51] Int. Cl.$^2$ .............................................. C07F 9/92
[52] U.S. Cl. ................................... 260/446; 208/120; 252/414; 252/426; 252/431 P; 252/456; 252/464
[58] Field of Search ........................................ 260/446

[56] References Cited

U.S. PATENT DOCUMENTS

| | | | |
|---|---|---|---|
| 2,777,874 | 1/1957 | Asseff et al. | 260/446 X |
| 2,951,086 | 8/1960 | Chadwick | 260/446 X |
| 3,412,118 | 11/1968 | Kujawa et al. | 260/446 X |
| 3,488,368 | 1/1970 | Spivack | 260/446 X |
| 3,773,815 | 11/1973 | Rossi et al. | 260/446 X |
| 4,083,860 | 4/1978 | Ruf | 260/446 X |

OTHER PUBLICATIONS

Chemical Abstracts, 67 65149h (1967).

*Primary Examiner*—Helen M. S. Sneed

[57] ABSTRACT

A cracking catalyst is treated with an antimony tris(dihydrocarbyl phosphite) to passivate contaminating metals whenever these metals have been deposited on the catalyst. Unused or used catalyst can be treated.

5 Claims, No Drawings

ANTIMONY TRIS(DIHYDROCARBYL PHOSPHITE) AND PREPARATION THEREOF

This invention relates to catalytic cracking of a hydrocarbon. In one of its aspects the invention relates to treating a catalyst to passivate contaminating metals whenever these metals appear on the catalyst. In another of its aspects the invention relates to a cracking catalyst which has been treated to passivate contaminating metals whenever these appear on the catalyst. In a further aspect, the invention relates to a process for the cracking of a hydrocarbon employing a catalyst which can be contaminated with metals tending to deactivate the same, the catalyst having been treated to passivate such metal or metals whenever these appear on the catalyst.

In one of its concepts the invention provides a method for treating a cracking catalyst to passivate contaminating metals whenever these appear on the catalyst by applying to the catalyst, used or unused, an antimony tris(dihydrocarbyl phosphite). In another of its concepts the invention provides a catalyst composition which has been modified or on which contaminating metals, whenever these appear thereon, have been passivated, the catalyst composition comprising a passivating amount of an antimony tris(dihydrocarbyl phosphite). In a further concept of the invention it provides a process for the cracking of the hydrocarbon employing a catalyst which has been modified or on which metals, when these appear thereon, have been passivated, as described herein.

Hydrocarbon feedstock containing higher molecular weight hydrocarbons is cracked by contacting it at an elevated temperature with a cracking catalyst whereby light distillates such as gasoline are produced. However, the cracking catalyst gradually deteriorates during this process. One reason for this deterioration is the deposition of contaminating metals such as nickel, vanadium, and iron on the catalyst, resulting in increased production of hydrogen and coke and decreased catalyst activity for cracking. Furthermore, the conversion of hydrocarbons into gasoline is reduced by these metals. Therefore, there is a need for a cracking process which will prevent or reduce the deleterious effects of these metal contaminants.

U.S. Pat. No. 3,711,422, Marvin M. Johnson and Donald C. Tabler, Jan. 16, 1973, discloses and claims restoring the activity of a cracking catalyst with a compound of antimony, e.g., antimony triphenyl. U.S. Pat. Nos. 4,025,458, May 24, 1977, and 4,031,002, June 21, 1977, Dwight L. McKay, disclose and claim passivating metals on a cracking catalyst with antimony compounds which are phosphorodithioates, as described in the patents.

It is an object of this invention to provide a method for passivating a catalyst having contaminating metals thereon. It is another object of the invention to treat a catalyst suitable for cracking a hydrocarbon, e.g., a hydrocarbon oil, to passivate contaminating metals, e.g., vanadium, iron and/or nickel, whenever these appear thereon, to render the same more effective for its intended use. It is a further object of the invention to produce a modified or treated catalyst suitable for cracking on which, whenever they appear, contaminating metals are passivated. It is a further object of the invention to provide an improved hydrocarbon cracking operation.

Other aspects, concepts, objects and the several advantages of the invention are apparent from a study of this disclosure and the appended claims.

According to the present invention a catalyst suitable for cracking hydrocarbon, e.g., a hydrocarbon oil, is treated by addition of an antimony tris(dihydrocarbyl phosphite) thereto so that whenever contaminating metals, e.g., vanadium, iron and/or nickel appear thereon, these will be passivated.

The catalyst treated can be a used or an unused catalyst.

Also according to the invention there is provided the thus-treated catalyst.

Still according to the invention there is provided a hydrocarbon cracking operation employing the modified or treated catalyst of the invention.

Thus, in accordance with this invention, a new or used conventional cracking catalyst is contacted with at least one antimony tris(dihydrocarbyl phosphite) to provide an antimony-containing cracking catalyst which is useful as a catalyst in the cracking of hydrocarbons containing a contaminating metal such as nickel, vanadium, or iron, the antimony in the catalyst serving to at least partially overcome the deleterious effects of the contaminating metals, regardless of whether these contaminating metals are present on the catalyst prior to contacting the catalyst with the antimony tris(dihydrocarbyl phosphite) or the contaminating metals are deposited from the metals-containing hydrocarbon feedstock onto the antimony-containing catalyst.

The cracking catalyst which is contacted with the antimony tris(dihydrocarbyl phosphite) can be any of those which are conventionally employed in the cracking of hydrocarbons boiling above about 400° F. (204° C.) for the production of motor fuel blending components and light distillates. These catalysts generally contain silica or silica-alumina, such materials frequently being associated with zeolitic materials. These zeolitic materials can be naturally occurring, or they can be produced by conventional ion exchange methods so as to provide metallic ions which improve the activity of the catalyst. Rare earth metals, including cerium, are frequently used for this purpose. Zeolite-modified silica-alumina catalysts are particularly applicable. Examples of cracking catalysts into which the antimony tris(dihydrocarbyl phosphite) can be incorporated include hydrocarbon-cracking catalysts obtained by admixing an inorganic oxide gel with an aluminosilicate and aluminosilicate compositions which are strongly acidic as a result of treatment with a fluid medium containing at least one rare earth metal cation and a hydrogen ion or ion capable of conversion to a hydrogen ion. If desired, the cracking catalyst can contain a combustion promoter such as platinum or chromium.

Antimony tris(dihydrocarbyl phosphite)s which can be employed in this invention can be represented by the formula $[(RO)_2PO]_3Sb$, where each R is selected from the group consisting of alkyl, cycloalkyl, and aryl, and combinations thereof such as alkaryl, aralkyl, and the like, the number of carbon atoms in each R being within the range of 1 to about 18.

Examples of some antimony tris(dihydrocarbyl phosphite)s which can be used include, antimony tris(dimethyl phosphite), antimony tris(diisobutyl phosphite), antimony tris(diethyl phosphite), antimony tris(dipropyl phosphite), antimony tris(dihexyl phosphite), antimony tris[bis(2-ethyloctyl) phosphite], antimony tris(dioctadecyl phosphite), antimony tris(dicyclohexyl phosphite), antimony tris[bis(3-methylcyclopentyl) phosphite], antimony tris[bis(cyclopentylmethyl) phosphite], an antimony tris-diphenyl phosphite) such as antimony tris(diphenyl phosphite) and antimony tris(di-p-tolyl phosphite); antimony tris(dibenzyl phosphite), antimony tris(butyl phenyl phosphite), antimony tris(dodecyl cyclohexyl phosphite), and the like, and mixtures thereof. Antimony tris(diphenyl phosphite) is the antimony tris(dihydrocarbyl phosphite) presently preferred.

Although any suitable procedure can be used, the preferred method for the preparation of the antimony tris(dihydrocarbyl phosphite)s comprises contacting in an aprotic solvent at least one alkali metal dihydrocarbyl phosphite having the formula $(RO)_2POM$, where each R is as defined above and M is an alkali metal selected from the group consisting of lithium, sodium, potassium, rubidium, and cesium, with at least one antimony compound having the formula $SbX_3$, where each X is selected from the group consisting of Cl, Br, I, —CN, —OCN, —SCN, and —OCOR', wherein each R' is selected from the group consisting of alkyl, cycloalkyl, and aryl, and combinations thereof such as alkaryl, aralkyl, and the like, the number of carbon atoms in R' being within the range of 1 to about 8.

Examples of some alkali metal dihydrocarbyl phosphites which can be used to produce the corresponding antimony tris(dihydrocarbyl phosphite)s include lithium dimethyl phosphite, sodium diethyl phosphite, potassium dipropyl phosphite, rubidium diisobutyl phosphite, cesium dihexyl phosphite, lithium bis(2-ethyloctyl) phosphite, sodium dioctadecyl phosphite, potassium dicyclohexyl phosphite, rubidium bis(3-methylcyclopentyl) phosphite, sodium bis(cyclopentylmethyl) phosphite, sodium diphenyl phosphite, lithium di-p-tolyl phosphite, potassium dibenzyl phosphite, cesium butyl phenyl phosphite, sodium dodecyl cyclohexyl phosphite, and the like, and mixtures thereof.

Examples of some antimony compounds having the formula $SbX_3$, where X is as defined above, which can be used in the preparation of the antimony tris(dihydrocarbyl phosphite)s include antimony trichloride, antimony tribromide, antimony chloride dibromide, antimony triiodide, antimony tricyanide, antimony tricyanate, antimony trithiocyanate, antimony triacetate, antimony tripropionate, antimony diacetate propionate, antimony tris(2-methylbutyrate), antimony trinonanoate, antimony tris(cyclohexanecarboxylate), antimony tris(3-methylcyclopentanecarboxylate), antimony tris(cyclopentylacetate), antimony tribenzoate, antimony tri-p-toluate, antimony tris(phenylacetate), and the like, and mixtures thereof. The aprotic solvent can be any aprotic solvent which is a liquid under the reaction conditions employed and which does not react with the reactants used or products formed.

Examples of some suitable aprotic solvents include hydrocarbons such as pentane, hexane, heptane, 2-methylheptane, decane, cyclohexane, methylcyclohexane, benzene, toluene, and o-xylene; ethers such as diethyl ether, dipropyl ether, dibutyl ether, and tetrahydrofuran; and ketones such as acetone, methyl ethyl ketone, diethyl ketone, dipropyl ketone, and cyclohexanone. Although the mole ratio of alkali metal dihydrocarbyl phosphite to antimony compound having the formula $SbX_3$, where X is as defined above, can vary considerably, e.g., from about 2:1 to about 5:1, preferably it is about 3:1. The weight ratio of aprotic solvent to antimony compound of formula $SbX_3$ can vary over a wide range but generally will be within the range of about 5:1 to about 100:1, preferably being within the range of about 10:1 to about 50:1. Although the reaction temperature is not critical, generally it will be within the range of about 10° C. to about 150° C., preferably being within the range of about 20° C. to about 100° C. The reaction time can vary greatly, depending in part on the reaction temperature, but generally will be within the range of about 5 minutes to about 8 hours, preferably being within the range of about 15 minutes to about 5 hours. The pressure should be sufficient to maintain the solvent substantially in the liquid phase. The antimony tris(dihydrocarbyl phosphite) can be isolated by conventional techniques such as filtration or extraction to separate it from by-product alkali metal salt. The solvent can be removed by ordinary techniques such as distillation. If desired, the solution of antimony tris(dihydrocarbyl phosphite), after removal of byproduct alkali metal salt, can be used to contact the conventional cracking catalyst, without prior separation of solvent from the solution, in the catalyst impregnation method described below.

The manner in which the conventional cracking catalyst is contacted with antimony tris(dihydrocarbyl phosphite) is not critical. For example, the antimony tris(dihydrocarbyl phosphite) in finely divided form can be mixed with conventional cracking catalyst in ordinary manner such as by rolling, shaking, stirring, or the like. Alternatively, a solution or dispersion of the antimony tris(dihydrocarbyl phosphite) in a suitable liquid, e.g., water, hydrocarbon, ether, or ketone, can be used to impregnate the conventional cracking catalyst, followed by volatilization of the liquid. If desired, the antimony tris(dihydrocarbyl phosphite) can be dissolved or dispersed in the hydrocarbon feedstock to the cracking process, in which instance the hydrocarbon feedstock and the antimony tris(dihydrocarbyl phosphite) contact the cracking catalyst at about the same time.

Although the ratio of antimony tris(dihydrocarbyl phosphite) to conventional cracking catalysts can vary over a wide range, depending in part on the concentration of contaminating metals in the catalyst and in the hydrocarbon feedstock to be cracked, the antimony tris(dihydrocarbyl phosphite) generally will be used in an amount such as to provide within the range of about 0.002 to about 5, preferably about 0.01 to about 1.5, parts by weight antimony per 100 parts by weight conventional cracking catalyst, i.e., including any contaminating metals in the catalyst but excluding the antimony tris(dihydrocarbyl phosphite).

The cracking process in which the antimony-containing cracking catalyst is employed is basically an improvement over a conventional cracking process which employs a conventional cracking catalyst. Although the antimony-containing cracking catalyst can be employed in a catalytic cracking process employing a fixed catalyst bed, it is especially useful in a fluid catalytic cracking process.

In a process for cracking topped crude oil containing metal contaminants a metals-contaminated cracking catalyst to which antimony has been added in the form of antimony tris(diphenyl phosphite) is more active and provides more gasoline, less coke, and less hydrogen than a comparable catalyst to which no antimony was added, and is even more active than a comparable catalyst to which antimony has been added in the form of antimony tris(0,0-dipropyl phosphorodithioate).

A preferred embodiment of the cracking process of this invention utilizes a cyclic flow of catalyst from a cracking zone to a regeneration zone. In this process, a hydrocarbon feedstock containing contaminating metals such as nickel, vanadium, or iron is contacted in a cracking zone under cracking conditions and in the absence of added hydrogen with an antimony-containing cracking catalyst produced by use of an antimony tris(dihydrocarbyl phosphite) as described above; a cracked product is obtained and recovered; the cracking catalyst is passed from the cracking zone into a regeneration zone; and in the regeneration zone the cracking catalyst is regenerated by contacting the cracking catalyst with a free oxygen-containing gas, preferably air. The coke that has been built up during the cracking process is thereby at least partially burned off the catalyst. The regenerated cracking catalyst is reintroduced into the cracking zone.

Furthermore, it is preferred in carrying out the cracking process of this invention to replace a fraction of the total cracking catalyst by unused cracking catalyst continuously or intermittently. Generally, about 0.5 to about 6 weight percent of the total cracking catalyst is replaced daily by a fresh cracking catalyst. The actual quantity of the catalyst replaced depends in part upon the nature of the feedstock used. The makeup quantity of cracking catalyst can be added at any location in the process. Preferably, however, the cracking catalyst that is makeup catalyst is introduced into the regenerator in a cyclic cracking process.

Also, it is to be understood that the used cracking catalyst coming from the cracking zone, before introduction into the regenerator, is stripped of essentially all entrained liquid or gaseous hydrocarbons. Similarly, the regenerated catalyst can be stripped of any entrained oxygen before it reenters the cracking zone. The stripping is generally done with steam.

The specific conditions in the cracking zone and in the regeneration zone are not critical and depend upon several parameters such as the feedstock used, the catalyst used, and the results desired. Preferably and most commonly, the cracking and regeneration conditions are within the following ranges:

| | Cracking Zone: |
|---|---|
| Temperature: | 800° F. to 1200° F. (427°–649° C.) |
| Time: | 1–40 seconds |
| Pressure: | Subatmospheric to 3,000 psig |
| Catalyst:Oil Ratio: | 3:1 to 30:1, by weight |
| | Regeneration Zone: |
| Temperature: | 1000° F. to 1500° F. (538° C. to 816° C.) |
| Time: | 2–70 minutes |
| Pressure: | Subatmospheric to 3,000 psig |
| Air @ 60° F. (16° C.) and 1 atm: | 100–250 ft³/lb coke (6.2–15.6 m³/kg coke) |

The feedstocks employed in the catalytic cracking process of this invention contain metal contaminants such as nickel, vanadium, and iron. The feedstocks include those which are conventionally utilized in catalytic cracking processes to produce gasoline and light distillate fractions from heavier hydrocarbon feedstocks. The feedstocks have an initial boiling point above about 400° F. (204° C.) and include fluids such as gas oils, fuel oils, topped crudes, shale oils, oils from tar sands, oils from coal, mixtures of two or more of these, and the like. By "topped crude" is meant those oils which are obtained as the bottoms of a crude oil fractionator. If desired, all or a portion of the feedstock can constitute an oil from which a portion of the metal content previously has been removed, e.g., by hydrotreating or solvent extraction.

Typically the feedstock utilized in the process of this invention will contain one or more of the metals nickel, vanadium, and iron within the ranges shown in Table I.

Table I

| Metal | Metal Content of Feedstocks, ppm[1] |
|---|---|
| Nickel | 0.02 to 100 |
| Vanadium | 0.02 to 500 |
| Iron | 0.02 to 500 |
| Total metals | 0.2 to 1100[2] |

[1]The ppm metal content refers to the feedstock as used.
[2]Total metals in this table and elsewhere refers to the sum of the nickel, vanadium, and iron contents in the feedstock that are effective in contaminating the catalyst; the total metals content can be determined in accordance with methods well known in the art, e.g., by atomic absorption spectroscopy.

One of the most important embodiments of this invention resides in a heavy oil cracking process. The known commercial heavy oil cracking process is capable of cracking heavy oils having a metals content of up to 80 ppm of total effective metals, i.e., metals in any form detrimental to the cracking process. Economically marginal results are obtained with oils having 40 to 80 ppm of total effective metals. In accordance with this invention, heavy oils with a total metals content of about 40 to 100 ppm and even those of about 100 to 200 ppm and above of total metals can be cracked in a cracking process in the absence of added hydrogen by utilizing the cracking catalyst defined above to yield gasoline and other fuels and fuel blending components. Thus, known heavy oils with total metals contents from 80 to 300 ppm that heretofore could not be directly used for fuel production and in particular for gasoline production in accordance with this invention can be cracked to yield gasoline and other fuel blending components. Most preferably the concentration of antimony in the antimony-containing cracking catalyst used in the process of this invention for cracking these heavily metal-loaded oils is related to the average total effective metals content of the feedstock as shown in Table II.

Table II

| Total Effective Metals in Feedstock, ppm | Antimony Concentration in Catalyst, Weight %[1] |
|---|---|
| 40–100 | 0.05–0.8 |
| 100–200 | 0.1–1 |
| 200–300 | 0.15–1.5 |
| 300–800 | 0.2–2 |

[1]Based on weight of catalyst prior to addition of antimony tris(dihydrocarbyl phosphite).

EXAMPLE I

Antimony tris(diphenyl phosphite) was produced by the reaction of diphenyl phosphite with sodium in benzene, followed by reaction of the resulting sodium diphenyl phosphite with antimony trichloride in benzene.

To 24.59 g (0.105 g-mole) diphenyl phosphite in 200 ml benzene at about 25° C. was added 2.30 g (0.10 g-atom) sodium metal. Hydrogen began to evolve immediately. After about 10 minutes, much of the evolution of hydrogen ceased, but a considerable amount of the sodium metal remained. The mixture was then refluxed for about 4 hours to give a brown slurry comprising sodium diphenyl phosphite in benzene. To this slurry at about 25° C. was added dropwise 7.60 g (0.033 g-mole) antimony trichloride in benzene. About two-thirds through this addition the solid phase became very dark. When the addition of antimony trichloride solution was complete, the resulting mixture was heated to reflux for about one-half hour, after which the nearly black mixture was allowed to cool to about 25° C. Filtration of the dark solids from the mixture gave 247.38 g of a nearly colorless benzene solution containing antimony tris(diphenyl phosphite) in a concentration calculated to be about 11.1 weight percent. A portion of this solution was used in the investigation described in Example II.

EXAMPLE II

A commercial cracking catalyst comprising amorphous silica-alumina associated with zeolitic material, which had been used in a commercial cracking unit and subsequently subjected to regeneration in the laboratory, was employed in tests which demonstrated the value of using antimony tris(diphenyl phosphite) in improving a cracking catalyst contaminated with metals detrimental to a cracking process. Properties of the used cracking catalyst prior to regeneration in the laboratory are shown in Table III.

Table III

| | |
|---|---|
| Surface area, m$^2$/g | 74.3 |
| Pore volume, ml/g | 0.29 |
| Composition, weight % | |
| Aluminum | 21.7 |
| Silicon | 24.6 |
| Nickel | 0.38 |
| Vanadium | 0.60 |
| Iron | 0.90 |
| Cerium | 0.40 |
| Sodium | 0.39 |
| Carbon | 0.06 |

The used commercial cracking catalyst having the properties shown in Table III was then subjected to regeneration in the laboratory by heating the catalyst while fluidized with air to 1200° F. (649° C.) and maintaining it at that temperature for about 0.5 hour while fluidized with air. The catalyst was then cooled to room temperature (about 25° C.) while fluidized with nitrogen, and the resulting catalyst, herein designated as catalyst O, was employed as shown below.

A portion of catalyst O was used in the preparation of a composition containing 0.5 part by weight antimony per 100 parts by weight catalyst O, the antimony being employed as antimony tris(diphenyl phosphite). In the preparation of this composition, 13.69 ml (10.67 g) of the benzene solution containing antimony tris(diphenyl phosphite) in a concentration of about 11.1 weight percent (1.64 weight percent antimony content), from Example I, was added to 25 ml benzene, and the resulting solution was stirred into 35.0 g of catalyst O. The mixture was then dried on a hot plate at 500° F. (260° C.). The resulting dried catalyst composition was transferred to a quartz reactor and heated to 900° F. (482° C.) as a bed fluidized with nitrogen, then heated to 1200° F. (649° C.) while fluidized with hydrogen, then purged with nitrogen for 5 minutes, and then purged with air for 15 minutes. The resulting catalyst composition was then preaged by processing it through ten reducing-oxidizing cycles wherein in each cycle the catalyst composition was cooled from 1200° F. (649° C.) to 900° F. (482° C.) during 0.5 minute while fluidized with air, then maintained at 900° F. (482° C.) for 1 minute while fluidized with nitrogen, then heated to 1200° F. (649° C.) during 2 minutes while fluidized with hydrogen, then maintained at 1200° F. (649° C.) for 1 minute while fluidized with nitrogen, and then maintained at 1200° F. (649° C.) for 10 minutes while fluidized with air. The catalyst composition was then cooled to room temperature (about 25° C.) while fluidized with nitrogen. The resulting catalyst composition is herein designated as catalyst AT.

A second portion of catalyst O was used in the preparation of a composition containing 0.5 part by weight antimony per 100 parts by weight catalyst O, the antimony being employed as antimony tris(O,O-dipropyl phosphorodithioate). In this preparation catalyst O, after being dried in a fluid bed at 900° F. (482° C.), was mixed with the calculated amount of a cyclohexanemineral oil solution of antimony tris(O,O-dipropyl phosphorodithioate) containing 0.0147 g antimony per ml solution. The treated catalyst was then heated to apparent dryness, after which the dried catalyst composition was transferred to a quartz reactor and heated to 900° F. (482° C.) as a bed fluidized with nitrogen, followed by regeneration at 1100° F. (593° C.) while fluidized with air. The catalyst composition was then preaged by processing it through ten cracking-regeneration cycles as a confined fluid bed in a quartz reactor using topped West Texas crude oil as feed. Each cycle consisted of a nominal 0.5-minute oil feed time to the catalyst fluidized with nitrogen during the cracking step conducted at about 950° F. (510° C.), followed by stripping of hydrocarbons from the system by fluidization of the catalyst for 3 to 5 minutes with nitrogen, followed by regeneration of the catalyst while heating to about 1200° F. (649° C.) for about 1 hour while fluidized with air. The catalyst was then cooled to room temperature (about 25° C.) while fluidized with nitrogen to provide a catalyst herein designated as catalyst ATDP.

Although the procedures used in the preparation of catalysts O, ATDP, and AT included some variations other than the use or lack of use of a particular modifying agent comprising antimony, these other variations were not such as would be expected to have a significant effect on the results obtained in the subsequent evaluation of the catalysts in cracking tests.

Catalysts O, ATDP, and AT were evaluated in three series of cracking-regeneration cycles, in which the cracking step was conducted over a range of catalyst:oil ratios, using approximately 33-35 g of catalyst as a confined fluid bed in a quartz reactor and employing topped West Texas crude oil as the feedstock in the cracking step. In each cycle the cracking step was carried out at 950° F. (510° C.) and about atmospheric pressure for 0.5 minute, and the regeneration step was conducted at about 1200° F. (649° C.) and about atmospheric pressure for approximately 1 hour using fluidizing air, the reactor being purged with nitrogen before and after each cracking step.

Properties of the topped West Texas crude oil used in this Example are shown in Table IV.

Table IV

| | |
|---|---|
| API gravity @ 60° F. (16° C.)[1] | 21.4 |
| Distillation, °F. (°C.)[2] | |
| IBP | 556 (291) |
| 10% | 803 (428) |
| 20% | 875 (468) |
| 30% | 929 (498) |
| 40% | 982 (528) |
| 50% | 1031 (555) |
| Carbon residue, Rams, wt %[3] | 5.5 |
| Elemental analysis | |

Table IV-continued

| | |
|---|---|
| S, wt % | 1.2 |
| Ni, ppm | 5.24 |
| V, ppm | 5.29 |
| Fe, ppm | 29 |
| Pour point, °F. (°C.)[4] | 63 (17) |
| Kinematic viscosity, cSt[5] | |
| @ 180° F. (82° C.) | 56.5 |
| @ 210° F. (99° C.) | 32.1 |
| Refractive index @ 67° C.[6] | 1.5 |

[1] ASTM D 287-67
[2] ASTM D 1160-61
[3] ASTM D 524-64
[4] ASTM D 97-66
[5] ASTM D 445-65
[6] ASTM D 1747-62

Typical results of the cracking tests are summarized in Table V. The conversion and yield results shown were determined graphically from curves which were drawn to represent values for conversion and yields as determined experimentally at the various catalyst:oil ratios employed.

Table V

| Catalyst | Catalyst: Oil Wt. Ratio | Conversion, Vol. % of Feed | Yield | | |
|---|---|---|---|---|---|
| | | | Gasoline Vol. % of Feed | Coke, Wt. % of Feed | H$_2$, SCF/bbl Feed Converted |
| 0 | 7.4 | 75 | 54.8 | 16.4 | 800 |
| ATDP | 7.4 | 75.8 | 63.4 | 12.1 | 330 |
| AT | 7.4 | 77.4 | 61.7 | 12.2 | 364 |

Thus, at essentially the same catalyst:oil weight ratio, the catalyst prepared by use of antimony tris(diphenyl phosphite), when compared with the catalyst prepared by use of antimony tris(O,O-dipropyl phosphorodithioate), provided higher feed conversion, and gave a high yield of gasoline and low levels of coke and hydrogen which were markedly superior to those obtained with the catalyst to which no antimony had been added.

Reasonable variation and modification are possible within the scope of the foregoing disclosure and the appended claims to the invention the essence of which is that there have been provided a novel antimony compound, i.e., an antimony tris(dihydrocarbyl phosphite), and that it has been found useful to passivate contaminating metals on a cracking catalyst employed for the cracking of a hydrocarbon, as described.

We claim:

1. An antimony tris(dihydrocarbyl phosphite).
2. An antimony tris(diphenyl phosphite).
3. Antimony tris(diphenyl phosphite).
4. A process for the preparation of an antimony tris(dihydrocarbyl phosphite) which comprises contacting in a suitable solvent at least one alkali metal dihydrocarbyl phosphite with at least one antimony compound having the formula SbX$_3$, where each X is selected from the group consisting of Cl, Br, I, —CN, —OCN, —SCN, and —OCOR', wherein each R' is selected from the group consisting of alkyl, cycloalkyl, and aryl, and combinations thereof such as alkaryl, aralkyl, the number of carbon atoms in R' being within the range of 1 to about 8.
5. A process according to claim 4 wherein the antimony compound produced is is antimony tris(diphenyl phosphite).

* * * * *